United States Patent
Engeberg

(10) Patent No.: US 10,543,111 B2
(45) Date of Patent: Jan. 28, 2020

(54) BIOMIMETIC CONTROLLER FOR INCREASED DEXTERITY PROSTHESIS

(71) Applicant: Erik Engeberg, Cuyahoga Falls, OH (US)

(72) Inventor: Erik Engeberg, Cuyahoga Falls, OH (US)

(73) Assignee: THE UNIVERSITY OF AKRON, Akron, OH (US)

( * ) Notice: Subject to any disclaimer, the term of this patent is extended or adjusted under 35 U.S.C. 154(b) by 0 days.

(21) Appl. No.: 14/075,175

(22) Filed: Nov. 8, 2013

(65) Prior Publication Data

US 2014/0128992 A1    May 8, 2014

Related U.S. Application Data

(60) Provisional application No. 61/724,053, filed on Nov. 8, 2012.

(51) Int. Cl.
| | | |
|---|---|---|
| *A61F 2/72* | (2006.01) | |
| *A61F 2/68* | (2006.01) | |
| *B25J 9/16* | (2006.01) | |
| *A61F 2/70* | (2006.01) | |

(52) U.S. Cl.
CPC .................... *A61F 2/72* (2013.01); *A61F 2/68* (2013.01); *A61F 2/70* (2013.01); *B25J 9/1612* (2013.01)

(58) Field of Classification Search
CPC .................... A61F 2/68; A61F 2/72
USPC ................................ 623/57, 61, 62
See application file for complete search history.

(56) References Cited

U.S. PATENT DOCUMENTS

| | | | | |
|---|---|---|---|---|
| 3,418,662 A | * | 12/1968 | Bottomley et al. ............. 623/25 |
| 3,883,900 A | * | 5/1975 | Jerard ........................ A61F 2/58 |
| | | | | 623/25 |
| 4,314,379 A | * | 2/1982 | Tanie et al. ..................... 623/25 |
| 5,336,269 A | * | 8/1994 | Smits ........................ A61F 2/72 |
| | | | | 623/24 |
| 5,888,213 A | * | 3/1999 | Sears ........................ A61F 2/68 |
| | | | | 623/24 |
| 6,379,393 B1 | * | 4/2002 | Mavroidis et al. ............. 623/25 |

(Continued)

OTHER PUBLICATIONS

Dalley et al. "A method for teh control of multigrasp myoelectric prosthetic hands", Jan. 2011, IEEE Trans Neural Syst Rehabil Eng., 20(1):58-67 (Year: 2012).*

*Primary Examiner* — Jacqueline Woznicki
(74) *Attorney, Agent, or Firm* — Renner Kenner Greive Bobak Taylor and Weber; Ray Weber; Tim Hodgkiss

(57) ABSTRACT

A sliding mode biomimetic (BSM) controller for a prosthetic device, such as a prosthetic hand, includes an input classification component that receives electromyogram (EGM) signals from two or more electromyogram (EGM) sensors that are positioned on an amputee's body. The input classification component compares the EGM input signals based on predetermined activation threshold values and identifies an input class to determine the amputee's intended movement of the prosthetic device. A finite state machine utilizes the current position of the prosthetic hand and the identified input class to identify the coordinates of a lookup table to determine the next state or position of the prosthetic device. As a result, the biomimetic controller is able to simultaneously control two or more degrees of freedom (DOFs) or functions of the prosthetic hand using only two EGM input signals.

11 Claims, 5 Drawing Sheets

(56) References Cited

U.S. PATENT DOCUMENTS

| | | | | |
|---|---|---|---|---|
| 2008/0243265 A1* | 10/2008 | Lanier | ............ | A61F 2/583 623/24 |
| 2010/0268351 A1* | 10/2010 | van der Merwe | ..... | G05B 15/02 623/24 |
| 2012/0150321 A1* | 6/2012 | Goldfarb | ............ | A61F 2/583 623/57 |

* cited by examiner

| State | Rest Position.($C_0$) | Large Ext. ($C_1$) | Flexion ($C_2$) | Light Ext. ($G_3$) | Cocontraction($C_4$) |
|---|---|---|---|---|---|
| I | FF,MF,RF,LF,TH $\theta_d = \theta_{II}$ $\theta_{WR} = 0°$ | FF,MF,RF,LF,TH,WR $\theta_d = 0°$ $\theta_{WR} = -K_eEMG_1$ GO TO STATE I | WR $\theta_d = \theta_{II}$ $\theta_{WR} = K_fEMG_2$ NO ACTION | FF,MF,RF,LF,TH $\theta_d = \theta_{II} - K_oEMG_1$ $\theta_{WR} = 0°$ | |
| II | FF,MF,RF,LF,TH $\theta_d = \theta_{III}$ $\theta_{WR} = 30°$ | $\theta_d = \theta_{III}$ $\theta_{WR} = 0°$ NO ACTION | $\theta_d = \theta_{III}$ $\theta_{WR} = 30°$ | FF,MF,RF,LF,TH $\theta_d = \theta_{III} - K_oEMG_1$ $\theta_{WR} = 30°$ | |
| III | FF,MF,RF,LF,TH $\theta_d = \theta_{III}$ $\theta_{WR} = -35°$ | $\theta_d = \theta_{III}$ $\theta_{WR} = -35°$ GO TO PREV. STATE | FF $\theta_d = \theta_{III}$ $\theta_{WR} = 0°$ GO TO STATE I | NO ACTION | $\theta_d = \theta_{IH} + K_{g1}EMG_1 + K_{g2}EMG_2$ $\theta_{WR} = K_2EMG_2 - K_1EMG_1$ |
| IV | FF,TH $\theta_d = \theta_{IVi}$ | $\theta_d = \theta_{prev}$ | FF,TH $\theta_d = \theta_{IVi} + K_eEMG_2$ | $\theta_d = \theta_{IVi}$ NO ACTION | FF,TH $\theta_d = \theta_{IVi} + K_{g1}EMG_1 + K_{g2}EMG_2$ |

FIG-3

BIOMIMETIC CONTROLLER FOR INCREASED DEXTERITY PROSTHESIS

CROSS-REFERENCE TO RELATED APPLICATION

This application claims the benefit of U.S. Provisional Application No. 61/724,053 filed on Nov. 8, 2012, the content of which is incorporated herein by reference.

TECHNICAL FIELD

Generally, the present invention relates to prosthetic devices. In particular, the present invention is directed to a biomimetic controller used to control a prosthetic device in a natural and physiologically expected manner. More particularly, the present invention is directed to a biomimetic sliding mode (BSM) controller that utilizes at least two electromyogram (EMG) muscle signals to simultaneously control two or more degrees of freedom (DOF) or functions of a prosthetic device.

BACKGROUND ART

Current prosthetic devices, such as prosthetic hands, are often controlled by electromyogram (EMG) muscle signals from an amputee who is fitted with the prosthetic device. The EMG signals are generally measured on the surface of the skin of the amputee and used for proportional control of various motors used to actuate various functions of the prosthetic device. That is, the voltage related to the muscle contraction defined by the EMG signal is measured, using suitable sensors, and then processed to control various motors or actuators to move the prosthetic device in a desired manner. For example, in the case of an amputee having a transradial or transcarpal amputation, one EMG pre-amplifier may be placed on the anterior compartment of the forearm, and a second EMG pre-amplifier is placed on the posterior compartment of the forearm. The signals from these two antagonistic muscles are amplified, filtered, rectified, and then given opposite algebraic signs, so that activation of the extensor muscles causes the prosthetic hand to open, while activation of the flexor muscles causes the prosthetic hand to close.

Although many different approaches to EMG signal processing have been developed, few have been commercially available for prosthetic devices. For example, numerous EMG signal processing techniques have been proposed for use in prosthetic devices, including: feature extraction, neural networks, and wavelet transforms. Such techniques have been previously utilized to classify EMG signal patterns and to obtain greater accuracy in decoding the amputee's intended movement of the prosthetic device. Unfortunately, these techniques have several drawbacks, including the inability to provide the amputee with control over both position and force of the prosthetic device. For example, in one attempt to provide EMG processing for a prosthetic hand, individual prosthetic finger movements were able to be discerned with a 98% accuracy, but required 32 surface-EMG electrodes to be placed on the forearm of the amputee to attain such performance. Nonlinear control methods produce increased time delays in processing EMG signals and may also require a higher number of EMG electrodes, which are required to be triggered by the amputee's muscle control. Thus, it would be desirable to provide a control scheme to control a prosthetic device, such as a prosthetic hand, which can automate many functions of the prosthetic device, so as to reduce the cognitive burden of the amputee.

The design and control of a prosthetic device, such as a prosthetic hand, is very difficult, and while many advances have been made, the difference in performance between the human hand and the prosthetic hand is substantial. Furthermore, amputees generally desire that their prostheses function in an increasingly more natural and life-like manner that they can control intuitively. In fact, it is common for an amputee to become discouraged and reject the use of his or her prosthesis because of its minimal functionality and lack of intuitive operation.

In addition, current generation prostheses, such as hand prostheses, typically permit only one degree of freedom (DOF) or one function to be controlled, such that in the case of a hand prosthesis, it operates as a gripper that can only open or close to perform a pinch/grasp function. That is, current prosthetic devices require the use of two electromyogram (EMG) signals to control a single DOF or function of the prosthesis at a time. As a result, such current generation prostheses are unable to control multiple DOFs simultaneously, which substantially reduces the dexterity that prosthetic devices, particularly prosthetic hands, can achieve.

In contrast to prosthetic hands, robotic hand technology has progressed further and is much more sophisticated in its operation. For example, the GIFU Hand and the Shadow Robot Hand offer significantly more controllable joints and feedback signals than prosthetic hands. This is because robotic hands are not limited by the numerous design constraints that are imposed by prosthetic hands, which include the requirement that the prosthetic be low mass, have a highly robust mechanical design, be low cost, and have an intuitive human-machine control interface. However, most critically, the lack of an intuitive control system for which to control multiple DOFs of a prosthesis is a critical obstacle that prevents the technology of dexterous robotic hands from being integrated into prosthetic hands.

Therefore, there is a need for a biomimetic controller for a prosthetic device that enables multiple degrees of freedom (DOF) to be simultaneously controlled using at least two EMG signals. In addition, there is a need for a biomimetic controller and EMG signal interpretation algorithms that allow a prosthetic device to be controlled intuitively in a natural, physiologically expected manner.

SUMMARY OF THE INVENTION

In light of the foregoing, it is a first aspect of the present invention to provide a control system for a prosthetic device having at least two degrees of freedom, the control system comprising a controller adapted to be coupled to the prosthetic device and adapted to receive at least two electromyogram (EMG) signals, each signal being from different muscle groups of an individual, the controller configured to compute a first motion control signal and a second motion control signal, such that the first motion control signal is a scaled sum of the at least two EMG signals, and the second motion control signal is a scaled difference of the at least two EMG signals; wherein the first motion control signal and the second motion control signal simultaneously control the at least two degrees of freedom of the prosthetic device.

Another aspect of the present invention is to provide a method for controlling a prosthetic device having at least two degrees of freedom comprising providing a controller adapted to be interfaced with the prosthetic device, receiving at least two electromyogram (EMG) signals from different muscles of an individual at the controller, generating a first motion control signal defined as a scaled sum of the at least two EMG signals, generating a second motion control signal defined as a scaled difference of the at least two EMG signals, and controlling the prosthetic device using the first and second motion control signals to simultaneously control the at least two degrees of freedom.

Yet a further aspect of the present invention is to provide a method for controlling a prosthetic device having at least two degrees of freedom comprising providing a control system adapted to be coupled to a control interface of the prosthetic device, the control system including a first electromyography (EMG) sensor and a second electromyography (EMG) sensor that are adapted to be attached to the skin of the user to detect muscle contractions, the control system storing a first and a second activation threshold value, and a lookup table of a plurality of actuation positions of the prosthetic device that are each identified by an initial position of the prosthetic hand and one or more predetermined input classes; detecting a first electromyography signal at the first EMG sensor, and detecting a second electromyography signal at the second EMG sensor; comparing the magnitude of the first and second EMG signals to each of the first and second activation threshold values; identifying the input class based on the comparison step; determining the actuation position from the lookup table based on the identified input class and the initial position of the prosthetic device; and simultaneously controlling at least two degrees of freedom, so as to move the prosthetic device to the actuation position.

BRIEF DESCRIPTION OF THE DRAWINGS

These and other features and advantages of the present invention will become better understood with regard to the following description, appended claims, and accompanying drawings wherein:

FIG. 3 is a lookup table used by a finite state machine of the BSM controller to determine the state of the prosthetic hand and an active motor configuration (AMC) value used to change the position of the prosthetic hand in accordance with the concepts of the present invention;

DETAILED DESCRIPTION

Figure 1:
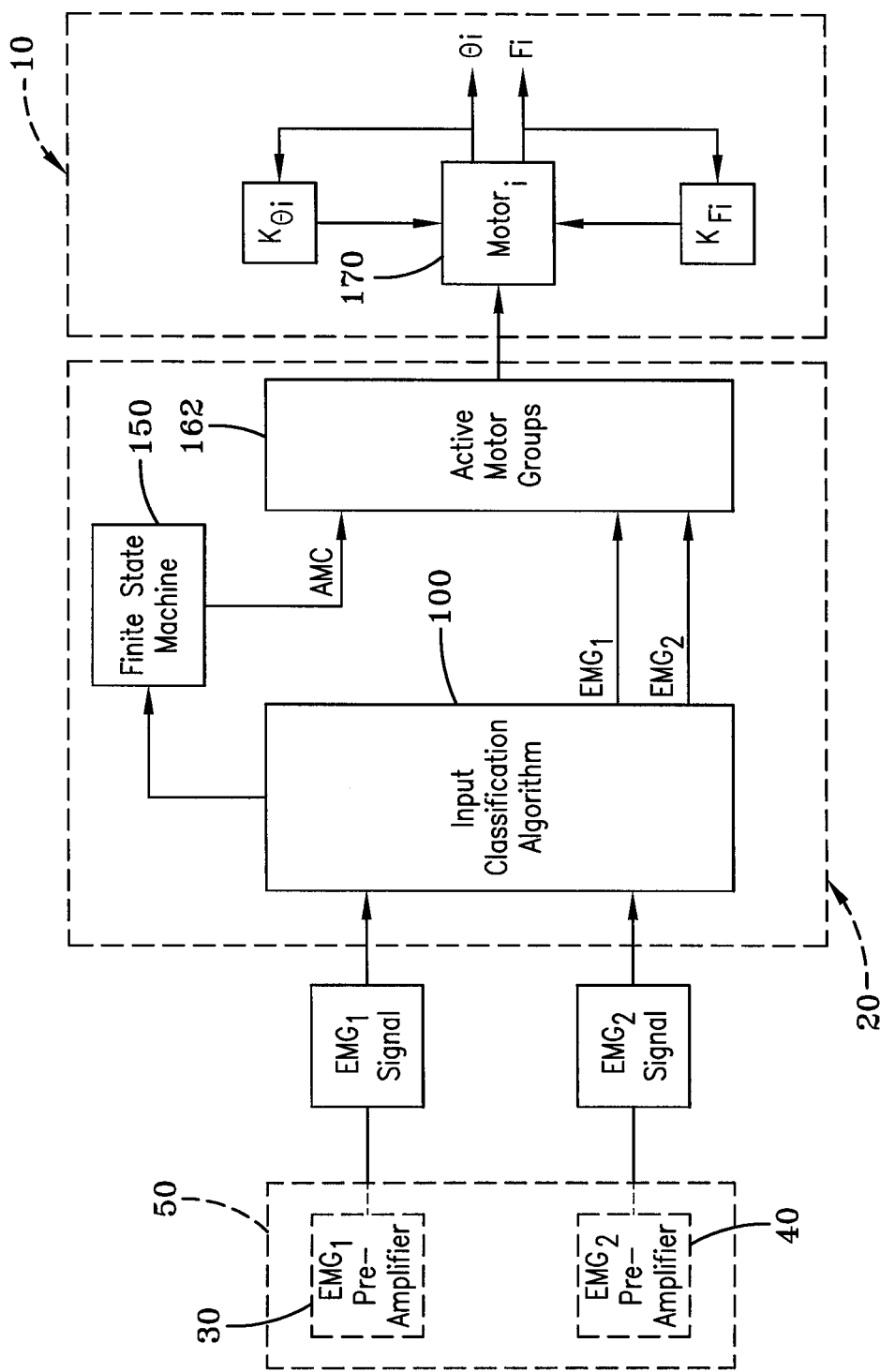
FIG. 1 is a block diagram of a biomimetic sliding mode (BSM) controller used to control a prosthetic device in accordance with the concepts of the present invention.

A biomimetic sliding mode (BSM) controller for use with a prosthetic device 10, such as a prosthetic hand, is generally referred to by numeral 20, as shown in FIG. 1 of the drawings. It should be appreciated that while the BSM controller 20 is discussed herein for use in controlling the prosthetic hand 10, the BSM controller 20 may be used to control any prosthesis or other electromechanical articulating apparatus, such as a robotic hand. Continuing, the prosthetic hand 10 may comprise any suitable prosthetic hand having at least two or more degrees of freedom (DOF).

Figure 2:
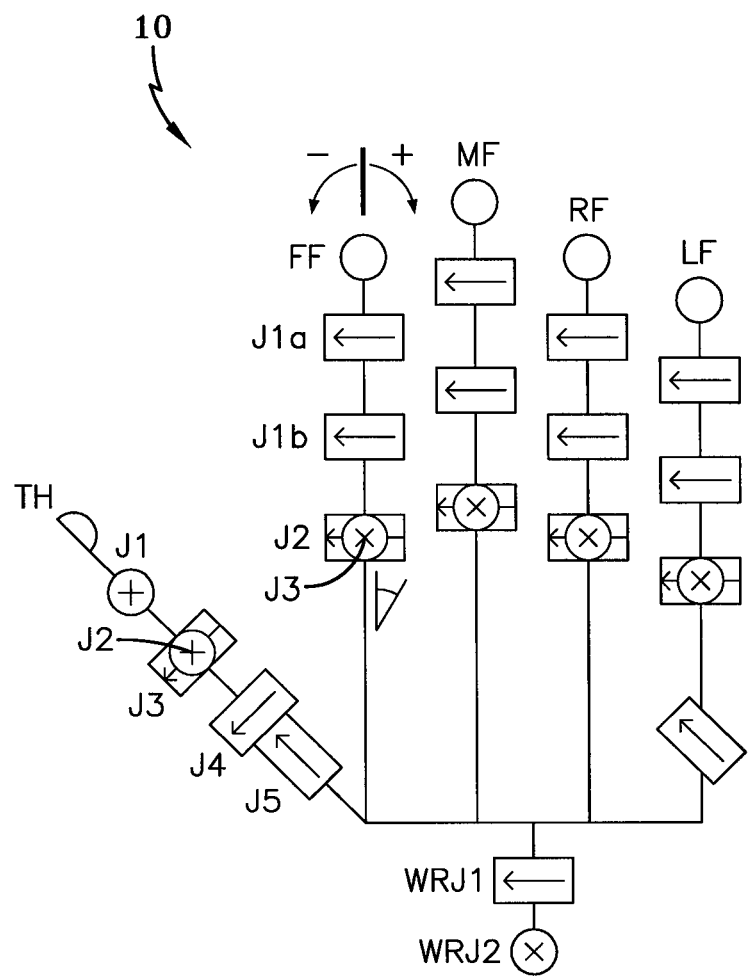
FIG. 2 is a block diagram showing the kinematic model of a prior-art prosthetic hand for use with a biomimetic sliding mode (BSM) controller of the present invention.

However, for the purposes of the following discussion, the prosthetic hand 10 comprises a SHADOW C6M motorized hand, manufactured by the Shadow Robot Company, in which its kinematic model is shown in FIG. 2. Specifically, the axes of rotation of the prosthetic hand 10 are identified as arrows, with axes of rotation perpendicular to the page being designated by an "X". Specifically, the prosthetic hand 10 includes a 24 joint, 20 degree of freedom (DOF) underactuated tendon-driven anthropomorphic manipulator. Hall effect sensors within the prosthetic hand 10 provide joint angle data for all 24 joints of the hand in real-time. The index, middle, and ring fingers each have four joints and three degrees of freedom (DOFs). The pinky finger has an extra DOF in the palm, modeling the metacarpophalangeal (MCP) joint. The distal interphalangeal joint (DIP) of each finger is kinematically coupled to the medial interphalangeal joint (MIP). The joints are driven by motors located below the wrist joint, with a pair of antagonistic tendons connecting each motor to the corresponding joint. The MIPs and DIPs of each finger of the prosthetic hand 10 are driven by a single motor and single pair of tendons. The system model of the prosthetic hand 10 is given by the equation:

$$B\ddot{\theta}+C\dot{\theta}+K\theta=\tau, \qquad (1)$$

where B and K are 20×20 matrices respectively representing the inertia and stiffness of the system. C is also a 20×20 matrix, which represents the damping of the system, as well as Coriolis and centrifugal terms. Vectors $\theta$, $\dot{\theta}$, and $\ddot{\theta}$ are 20×1 column vectors that represent the joint angular positions, velocities, and accelerations. The torque vector z is a function of the motor inputs and nonlinear disturbances of the prosthetic hand 10. Motor inputs are determined by embedded microcontrollers and are a function of the desired angle ($\theta_d$) and the current position ($\theta_i$) of the joint.

The naming convention of the joints of the prosthetic hand 10 is shown in FIG. 2, and because the DIP and MIP joints of each finger are coupled, they are referred to as joint J1$a$ and joint J1$b$, respectively. A virtual joint J1 is defined as the sum of joints J1$a$ and J1$b$, and control of both joints is defined as a parameter of joint J1.

Extension/Flexion of the proximal interphalangeal joint (PIP) of the prosthetic hand is defined as joint J2 and abduction of the PIP, as joint J3. Joints J2 and J3 are controlled by motors 2 and 3, respectively, and the DIP and MIP of each finger are both controlled by motor 1.

Differentiation between fingers of the prosthetic hand 10 is dictated by the designations FF, MF, RF, LF, and TH, which identify the index finger, middle finger, ring finger, little finger, and thumb, respectively. According to this convention, the DIP joint of the index finger is defined as FFJ1$a$, the MIP joint of the ring finger is defined as RFJ1$b$, and so forth. The wrist joint is also shown in FIG. 1 and is designated as WRJ1, which is negative in extension and positive in flexion.

The motors of the prosthetic hand 10 are separated into six motor groups, as set forth in Table I below. Specifically, each motor group comprises a number of actively controlled joints, where all joints, including those not listed in the motor groups, are passively controlled. That is, all joints have a desired angle that is set by the BSM controller 20, regardless of whether or not they are being actively controlled by the user.

TABLE I

Motor Groups

| Motor Group | Actively Controlled Joints |
| --- | --- |
| FF—Index Finger | FFJ1a, FFJ1b, FFJ2 |
| MF—Middle Finger | MFJ1a, MFJ1b, MFJ2 |
| RF—Ring Finger | RFJ1a, RFJ1b, RFJ2 |
| LF—Little Finger | LFJ1a, LFJ1b, LFJ2 |
| TH—Thumb | THJ1, THJ2 |
| WR—Wrist | WRJ1 |

Continuing, the BSM controller 20, and any components thereof, may comprise any suitable hardware, software, or a combination of both that is configured to carry out the functions to be discussed. Two electromyogram (EMG) preamplifiers or sensors 30 and 40 are coupled to the BSM controller 20 and are configured to be applied to the skin of the user to detect electrical impulses or signals that are associated with the contraction of various muscles of an amputee's body, such as his or her forearm 50 in the case of the present example. In one aspect, the EMG sensor 30 may be placed on an amputee's forearm 50 over its posterior compartment, which includes the extensor digitorum communis (EDC) muscle, while the sensor 40 may also be placed on an amputee's forearm 50 over its anterior compartment, which includes the flexor carpi radialis (FCR) muscle and the flexor digitorum superficialis (FDS) muscle. In other words, the EMG sensors 30 and 40 serve to detect EMG signals, which identify the contraction of particular muscles in an amputee's forearm 50, including the EDS, FCR, and FDS muscles. Once detected, the EMG sensors 30 and 40 amplify, filter, and rectify the detected EMG signals into processed EMG signals, designated as $EMG_1$ and $EMG_2$ respectively, using known techniques for subsequent processing by the BSM controller 20 in the manner to be discussed. It should also be appreciated that in other embodiments, the BSM controller 20 may be configured to utilize more than two EMG signals.

The BSM controller 20 includes an input classification algorithm component 100 that is coupled to the EMG sensors 30 and 40. The input classification algorithm component 30, which may comprise hardware, software, or a combination of both, receives the processed EMG signals, designated as $EMG_1$ and $EMG_2$, from the respective EMG sensors 30 and 40 via any suitable communication means, such as electrically-conductive wires, optical cables, or the like. It is also contemplated that the EMG sensors 30 and 40 may wirelessly communicate with the input classification algorithm component 100 using any suitable communication protocol, such as WIFI or BLUETOOTH for example. The input classification algorithm component 100 is programmed to normalize the processed EMG signals, $EMG_1$ and $EMG_2$, based on the maximum contraction that is possible to be recorded from each EMG sensor or preamplifier 30 and 40. It should be appreciated that the maximum contraction value is determined and programmed into the input classification algorithm component 100 prior to the use of the BSM controller 20. In addition, the classification algorithm component 100 is also configured to classify the normalized inputs into a plurality of input classes. For example, the input classification algorithm component 100 may classify the normalized inputs into five input classes, designated $C_0$-$C_4$, as shown in Table II, which are used to control the position and grip force of the prosthetic hand 10.

An activation threshold value, designated as $K_1$, is also programmed at the input classification algorithm component 100 and is set slightly above the noise threshold for each of the EMG input signals $EMG_1$ and $EMG_2$. Thus, when each of the EMG input signals $EMG_1$ and $EMG_2$ are below the $K_1$ threshold, the EMG input signals $EMG_1$ and $EMG_2$ are identified by the input classification algorithm component 100 as being equivalent to zero, which is designated by class $C_0$. A second threshold, $K_2$, is set above the noise threshold and distinguishes between a light and large contraction of each of the EDS, FCR, and FDS muscles of the forearm 50, to identify various other input classifications $C_1$-$C_4$ that are used by a state machine component 150 of the controller 20. For example, input classification $C_1$ designates a large extension of the prosthetic hand 10; input classification $C_2$ designates a flexion prosthetic hand 10; input classification $C_3$ designates a light extension prosthetic hand 10; and input classification $C_4$ designates a cocontraction prosthetic hand 10. It should also be appreciated that thresholds $K_1$ and $K_2$ are not necessarily the same for each of the EMG signals $EMG_1$ and $EMG_2$.

TABLE II

Classification of EMG Inputs

| Input Class | $EMG_1$ | $EMG_2$ |
| --- | --- | --- |
| Zero Input ($C_0$) | $EMG_1 < K_1$ | $EMG_2 < K_1$ |
| Large Extension ($C_1$) | $EMG_1 > K_2$ | $EMG_2 < K_1$ |
| Flexion ($C_2$) | $EMG_1 < K_1$ | $EMG_2 > K_1$ |
| Light Extension ($C_3$) | $K_1 < EMG_1 < K_2$ | $EMG_2 < K_1$ |
| Cocontraction ($C_4$) | $EMG_1 > K_1$ | $EMG_2 > K_1$ |

The finite state machine component 150 of the BSM controller 20 uses a lookup table 160, as shown in FIG. 3, to identify the manner in which the various degrees of freedom (DOF) of the prosthetic hand 10 are to be controlled. Specifically, each entry in the lookup table shown in FIG. 3, which is used by the finite state machine 150, is divided into a 4×1 vector. The top row in each vector defines the active motor groups or state transition; second row in each vector depicts the new position of the hand due to the input class; and the third row in each vector defines the desired angle for each joint in the actively controlled motor group(s) ($\theta_d$). Those joints not in the active motor group(s) remain in the rest position. The bottom row in each vector defines the wrist position ($\theta_{WR}$). $K_e$, $K_f$, $K_o$, $K_t$, $K_1$, $K_2$, $K_{g1}$, and $K_{g2}$ are all gains applied to each joint individually to obtain a response mimicking that of the human hand, and are not necessarily equal between joints.

Thus, the positional state of the prosthetic hand 10 and the input class are used as the coordinates of the lookup table 160, which determines both the state of the prosthetic hand 10 and an active motor configuration (AMC) value that enable the active motor group 162 to determine which motors 170 of the prosthetic hand 10 are to be active. The state defines the rest position ($\theta_i$, i=I, II, III, IV) for all finger joints of the prosthetic hand 10. This is the default position of the prosthetic hand 10, when the input classification is identified as $C_0$, indicating that the $EMG_1$ and $EMG_2$ signals are below the thresholds $K_1$ and $K_2$. The positions of the joints in the active motor groups (AMG) of the prosthetic hand 10 become functions of the rest position of the current state, as well as the normalized EMG inputs ($EMG_1$, $EMG_2$). These equations are represented in the third column of each entry of the lookup table 160 of FIG. 3. Those joints that are not in the active motor configuration (AMC) remain in their rest position that is defined by the state of the hand 10. The position of the wrist joint ($\theta_{WR}$) is controlled, as defined in the bottom row of each entry of the lookup table 160 for FIG. 3. This process is performed separately from and simultaneously with the control of the finger positions of the prosthetic hand 10, which are a function of the current state and the active motor configuration (AMC). In the case that the input class causes the state of the prosthetic hand 10 to change, the hand pauses, whereupon it is repositioned according to the new state, in accordance with the lookup table 160 of FIG. 3.

For states I, II, and III, the state defines the position of all controllable joints including the wrist (FIG. 3 (I-III, $C_0$). In these states, the rest position of the prosthetic hand 10 resembles a lightly-closed fist, with the thumb in opposition to the index and middle fingers. In state I, the amputee wearing the prosthetic hand 10 has proportional control of the wrist joint WRJ1. For input classes $C_1$ and $C_2$, the wrist extends or flexes proportionally to the EMG signals received by the controller 20. If the wrist is held at a fully-extended (−35 degrees) or fully-flexed (30 degrees) position for a period of about one second, the prosthetic hand transitions to state III or II, respectively, which locks the wrist in place either in a fully-extended or a fully-flexed position.

State IV provides a typing function [FIG. 3, (IV, $C_2$)] and a lateral pinch grasp function [FIG. 3, (IV, $C_4$)]. It defines the positions for all finger joints, but does not define wrist position [FIG. 3, (IV, $C_0$)]. State IV can be entered while the wrist is locked in the fully-flexed, neutral, or fully-extended positions. While in state IV, the thumb is brought in parallel with the palm of the hand 10, with the index finger fully extended and the remaining fingers flexed. State IV is entered from a light extension ($C_3$) for a period of two seconds and is exited by a large extension ($C_1$). Since wrist position is not defined directly through state IV, the position of the hand 10 reverts back to its previous state ($\theta_{prev}$) upon leaving state IV [FIG. 3, (IV, $C_1$)].

During force control (input class $C_4$) in states I, II, and III, the wrist angle of the prosthetic hand 10 can also be actively controlled. The desired angle of WRJ1 is determined by a weighted difference of signals $EMG_1$ and $EMG_2$. If the wrist is held in a fully-flexed (30 degrees) or fully-extended (−35 degrees) position for a period of time, such as one second, the prosthetic hand 10 enters state II or III, respectively.

Figure 4:
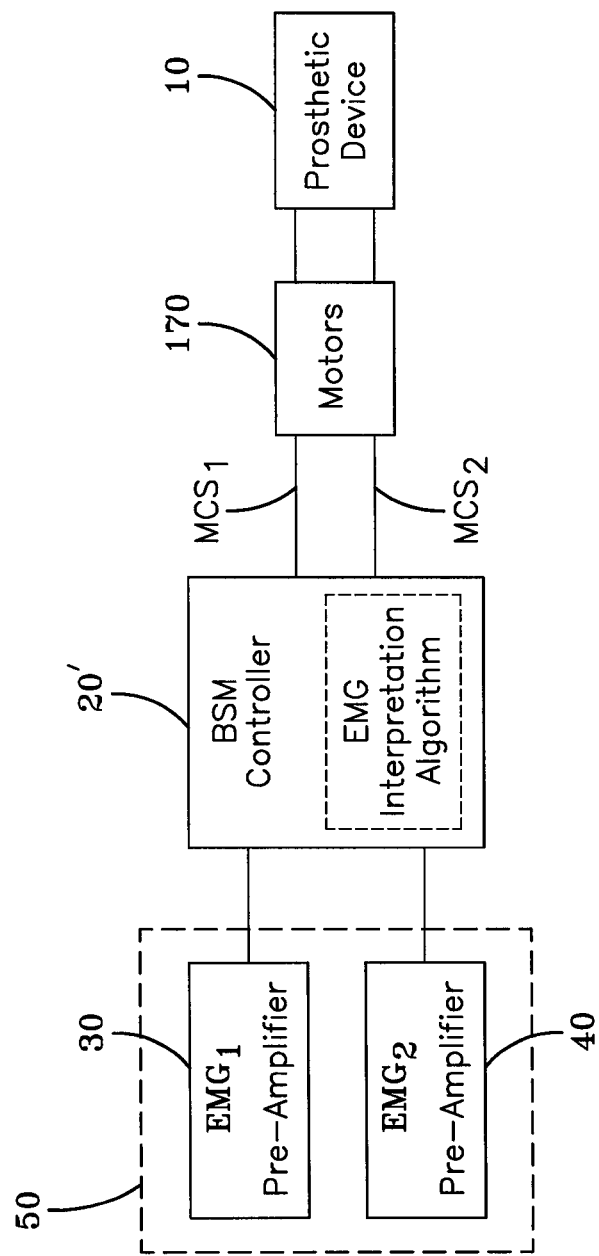
FIG. 4 is an alternative biomimetic sliding mode (BSM) controller used to control a prosthetic device, such as the prosthetic hand shown in FIG. 2.

In yet another embodiment, a biomimetic sliding mode (BSM) controller 20' used to simultaneously control any desired prosthesis having at least two degrees of freedom or at least two functions is coupled to the EMG pre-amplifiers or sensors 30 and 40, as shown in FIG. 4. The BSM controller 20' includes the necessary hardware, software, or combination of both to carry out the functions set forth below. As previously discussed, the $EMG_1$ and $EMG_2$ signals are filtered, rectified, and amplified using known techniques. The EMG signals are also normalized from zero to one according to prerecorded maximum and minimum muscle contraction levels of the amputee. In particular, the BSM controller 20' may comprise a signal processor that is configured or otherwise programmed to processes the $EMG_1$ and $EMG_2$ signals detected from the contractions of any two desired muscles or muscle groups of the amputee in accordance with an EMG interpretation algorithm component 300 to produce two separate motion control signals (MCSs) that are each capable of controlling of two or more degrees of freedom (DOF) of any motorized prosthetic device, such as the prosthetic hand 10. It should be appreciated that the EMG interpretation algorithm component 300 may be embodied in hardware, software, or a combination of both. For example, a first motion control signal output by the EMG interpretation algorithm component 300 may be used to control the grasping force of the DOFs of the hand portion of the prosthetic hand, while the second motion control signal output by the EMG interpretation algorithm component 300 may be used to control the position of the DOFs of the wrist portion of the prosthetic hand 10.

Specifically, the EMG interpretation algorithm component 300 used to generate the motion control signal $MCS_1$ and $MCS_2$ is defined by the following equations:

$$MCS_1 = K_1 * EMG_1 + K_2 * EMG_2 \qquad (2)$$

$$MCS_2 = K_1 * EMG_1 - K_2 * EMG_2 \qquad (3),$$

where $K_1$ and $K_2$ are predetermined gain values that are preprogrammed into the BSM controller 20'. As such, the motion control signal $MCS_1$ of eq. (2) is calculated as the scaled sum of the two EMG signals, $EMG_1$ and $EMG_2$, while the motion control signal $MCS_2$ of eq. (3) is calculated as the scaled difference between the two EMG signals, $EMG_1$ and $EMG_2$. It should also be appreciated that the gains $K_1$ and $K_2$ used in equation (2) may be different from those gains $K_1$ and $K_2$ in equation (3), depending on the particular individual needs of the amputee wearing the prosthetic device. These two motion control signals, $MCS_1$ and $MCS_2$, that are output by the BSM controller 20' are then supplied to the appropriate motors 170 or motor control interface prosthetic device 10. This allows the BSM controller 20' to simultaneously control two separate DOFs/functions or two separate groups of DOFs/functions therein of the prosthetic hand 10. It should be appreciated that because the two motion control signals, $MCS_1$ and $MCS_2$, each control a separate DOF/function, or a separate group of DOFs/functions of the prosthetic device 10, such functions can be performed simultaneously, which is highly desirable. For example, in the case of the prosthetic hand 10, both hand grasping force and wrist position may be simultaneously controlled; or in another example, both hand position and wrist torque may both be simultaneously controlled. Such ability substantially increases the dexterity, while enhancing the ability of the prosthetic device 10 to be intuitively controlled by the amputee.

Thus, in the case of the prosthetic hand 10, the $EMG_1$ and $EMG_2$ sensors may be used to respectively detect the extension (E) and flexion (F) of the muscles in an amputee's forearm 50, such that $EMG_1 = EMG_E$ and $EMG_2 = EMG_F$. The $EMG_E$ and $EMG_F$ signals are then scaled by predetermined gain values $K_1$ and $K_2$ to obtain the calculated motion control signals $MCS_1$ and $MCS_2$. The $MCS_1$ and $MCS_2$ signals are used to respectively control the grasping force of prosthetic hand 10 and the position of the wrist of the prosthetic hand 10 in a simultaneous manner. While this example sets forth the use of the controller 20' to simultaneously control the grasping force and wrist position of a prosthetic hand, it should be appreciated that the motor control signals $MCS_1$ and $MCS_2$ output by the controller 20' may be each used to independently control any desired DOF provided by any prosthetic device. Furthermore, the independent control of two DOFs of the prosthesis, thereby allows the independent control of any two functions provided by the prosthesis, such as a typing function and a pinching function, or such as a wrist position and gripping force function for example.

For example, in state IV shown in FIG. 3, equation (2) can be used to control the pinch force of the prosthetic hand 10 that is exerted by the thumb opposing the index finger. In this same configuration, equation (3) can be used to control the position of the index finger, enabling a typing or tapping function. This same concept can be can be extended to the simultaneous control of any two DOFs or functions provided by a prosthetic device, such as a prosthetic hand, grip force and wrist motion, as depicted in states I-III of FIG. 3. In any of these states, equation (2) controls the grip force of the hand, while equation (3) simultaneously controls the wrist position. The advantage of the BM controller 20' of the present invention is that the two electromyogram signals or inputs, $EMG_1$ and $EMG_2$, are used to simultaneously control two functions or DOFs of the prosthetic device 10.

Figure 5:
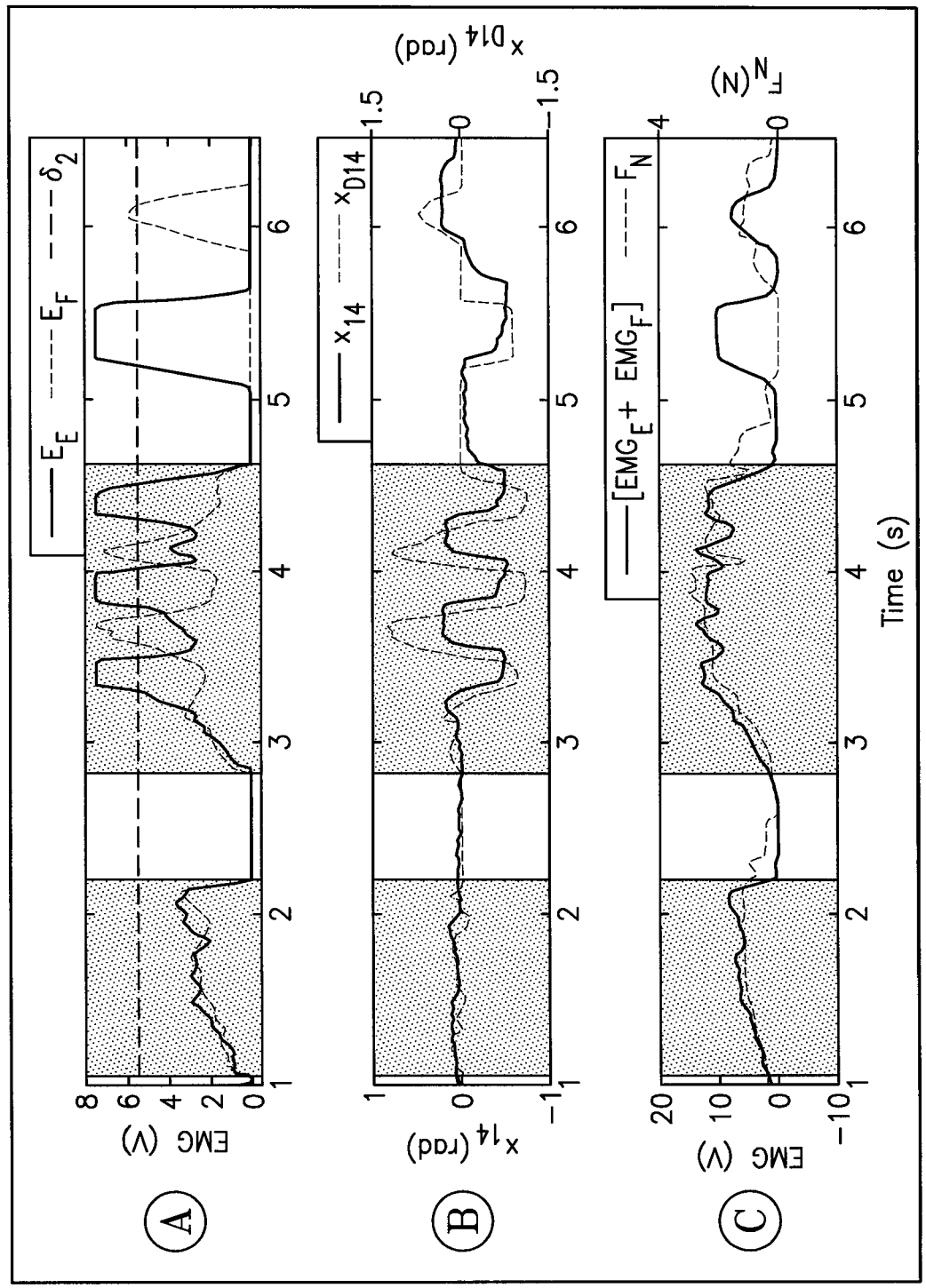
FIGS. 5A-C are graphs showing the electromyogram (EMG) signals driving the biomimetic sliding mode (BSM) controller for the prosthetic hand shown in FIGS. 2 and 3.

The ability of the BSM controller 20' to simultaneously control two or more degrees of freedom (DOF) of a prosthetic device was evaluated experimentally, as shown in FIGS. 5A-C. Specifically, FIG. 5 shows the control of the prosthetic hand 10 under the control of the BSM controller 20', whereby when the EMG signals $EMG_E$ (designated as $E_E$ in FIG. 5A) and $EMG_F$ (designated as $E_F$ in FIG. 5A) are simultaneously increased at the beginning of the experiment, the measured grip force ($F_N$), shown in FIG. 5C, increases as the motion control signal $MCS_1$ from equation (2) is used to specify the desired grip force of the prosthetic hand 10. Next, both EMG signals $EMG_E$ and $EMG_F$ are relaxed, and the measured grip force returns to zero. In the third phase of the experimental evaluation, the simultaneous control of wrist position and grip force of the prosthetic hand 10 is demonstrated. As previously discussed, the grip force increases when the motion control signal $MCS_1$ increases, due to the cocontraction of $EMG_E$ and $EMG_F$. However, the measured wrist angle of the prosthetic hand 10, denoted as $X_{14}$=WRJ1, initially remains at zero because the motion control signal $MCS_2$ of equation (3) is used to specify the desired position of the wrist, denoted as $X_{D14}$, as shown in FIG. 5B. In addition, motion control signal $MCS_2$ remains at approximately zero because the EMG signals cancel each other out, in accordance with equation (3). However, further alternating contractions defined by $EMG_E$ or $EMG_F$ drives the wrist angle $X_{14}$ to move forward and backward as equation (3) becomes positive or negative. Simultaneously, in this circumstance, the desired grip force specified by motion control signal $MCS_1$ from equation (2) remains positive, which is why the measured grip force remains positive. This demonstrates the ability of the BSM controller 20 to simultaneously control the grip force and wrist position (i.e. 2 separate DOFs or functions). However, wrist position can also be controlled independently without any applied grip force, as is illustrated in FIG. 5C. Specifically, when $EMG_E$ is increased, while $EMG_F$ is relaxed (i.e. maintained near zero), the wrist motion of the prosthetic hand 10 is controlled via equation (3), but the grip force is not increased because both $EMG_E$ (i.e $EMG_1$) and $EMG_F$ (i.e. $EMG_2$) are not both simultaneously above the specified threshold level indicated in Table II.

Based on the foregoing, one advantage of the present invention is that a biomimetic sliding mode (BSM) controller is able to process two or more electromyogram (EGM) signals to simultaneously control two or more degrees of freedom (DOF) or functions of a prosthetic device, such as a prosthetic hand, thereby increasing its dexterity and providing more lifelike and natural motion and control of the prosthetic hand. Still another advantage of the present invention is that the biomimetic sliding mode (BSM) controller is able to be utilized with the EGM control interface of current generation prosthetic hands. Another advantage of the present invention is that the biomimetic sliding mode (BSM) controller operates in a non-linear manner, thereby allowing a prosthetic device to have stable operating performance, even in the presence of external disturbances. An additional advantage of the present invention is that the biomimetic sliding mode (BSM) controller allows an amputee to have intuitive control over the prosthetic device, allowing it to be controlled in a natural, physiologically expected manner, with increased dexterity. In addition, a further advantage of the present invention is that the biomimetic sliding mode (BSM) controller reduces the training time for amputees in controlling a prosthetic device.

Thus, it can be seen that the objects of the invention have been satisfied by the structure and its method for use presented above. While in accordance with the Patent Statutes, only the best mode and preferred embodiment has been presented and described in detail, it is to be understood that the invention is not limited thereto or thereby. Accordingly, for an appreciation of the true scope and breadth of the invention, reference should be made to the following claims.

What is claimed is:

1. A control system for a prosthetic hand having a wrist, a plurality of fingers and a thumb, with the wrist having a first degree of freedom, at least one of the plurality of fingers having a second degree of freedom, and the thumb having a third degree of freedom, the control system comprising:
a controller adapted to be coupled to the prosthetic hand, and adapted to receive a first and a second electromyogram (EMG) signal, each said signal being from different muscle groups of an individual; and
an input classification algorithm component provided by said controller, which compares said first EMG signal and said second EMG signal to a first and a second threshold value, wherein based on the comparisons a first control signal comprising a weighted sum of said first and second EMG signals and a second control signal comprising a weighted difference of said first and second EMG signals are generated, and one of a plurality of input classes that identifies a new position of the prosthetic hand is selected;
and
wherein said first and second EMG control signals simultaneously control at least two of the first, second and third degrees of freedom in accordance with the new position of the prosthetic hand.

2. The control system of claim 1, wherein said comparisons are performed simultaneously.

3. The control system of claim 1, wherein said input classes includes an extension, a flexion, a light extension and a co-contraction.

4. The control system of claim 1, wherein said control of the first degree of freedom provided by the wrist controls a torque thereof.

5. The control system of claim 1, wherein the first, second and third degrees of freedom are controlled simultaneously.

6. A method for controlling a prosthetic hand having a wrist, a plurality of fingers and a thumb, such that the wrist has a first degree of freedom, at least one of the plurality of fingers has a second degree of freedom, and the thumb has a third degree of freedom comprising:
providing a controller adapted to be interfaced with the prosthetic hand;
receiving a first and a second electromyogram (EMG) signal from different muscle groups of an individual at said controller;
comparing said first EMG signal to a first and a second threshold value;
comparing said second EMG signal to said first and second threshold values;
generating a first control signal comprising a weighted sum of said first and second EMG signals and generating a second control signal comprising a weighted difference of said first and second EMG signals;

selecting one of a plurality of input classes based on said comparisons to identify a new position of the prosthetic hand; and simultaneously controlling, using the first and second control signals, at least two of the first, second and third degrees of freedom in accordance with the new position of the prosthetic hand that has been selected said selected input class.

7. The method of claim 6, wherein the second and third degrees of freedom are controlled to adjust a grip force of the prosthetic hand.

8. The method of claim 6, wherein said comparisons are performed simultaneously.

9. The method of claim 6, wherein said input classes includes an extension, a flexion, a light extension and a co-contraction.

10. The method of claim 6, wherein said controlling step of the first degree of freedom provided by the wrist controls a torque thereof.

11. The method of claim 6, wherein the first, second and third degrees of freedom are controlled simultaneously.

* * * * *

UNITED STATES PATENT AND TRADEMARK OFFICE
CERTIFICATE OF CORRECTION

PATENT NO. : 10,543,111 B2
APPLICATION NO. : 14/075175
DATED : January 28, 2020
INVENTOR(S) : Erik Engeberg Page 1 of 1

It is certified that error appears in the above-identified patent and that said Letters Patent is hereby corrected as shown below:

In the Claims

At Column 10, Line 38, after "wherein said first and second" delete "EMG".

Signed and Sealed this
Seventeenth Day of March, 2020

Andrei Iancu
*Director of the United States Patent and Trademark Office*